US012121340B2

(12) United States Patent
van Niekerk

(10) Patent No.: US 12,121,340 B2
(45) Date of Patent: Oct. 22, 2024

(54) WIRELESS RADIO FREQUENCY TRIGGERED SIGNAL ACQUISITION DEVICE

(71) Applicant: University of Cape Town, Cape Town (CA)

(72) Inventor: Adam Marthinus Johannes van Niekerk, Claremont (CA)

(73) Assignee: University of Cape Town, Cape Town (ZA)

( * ) Notice: Subject to any disclaimer, the term of this patent is extended or adjusted under 35 U.S.C. 154(b) by 782 days.

(21) Appl. No.: 17/055,642

(22) PCT Filed: Jun. 5, 2019

(86) PCT No.: PCT/IB2019/054675
§ 371 (c)(1),
(2) Date: Nov. 16, 2020

(87) PCT Pub. No.: WO2019/239256
PCT Pub. Date: Dec. 19, 2019

(65) Prior Publication Data
US 2021/0212588 A1    Jul. 15, 2021

(30) Foreign Application Priority Data
Jun. 15, 2018    (GB) ..................... 1809866

(51) Int. Cl.
*A61B 5/055*    (2006.01)
*A61B 5/00*    (2006.01)
(Continued)

(52) U.S. Cl.
CPC .............. *A61B 5/055* (2013.01); *A61B 5/062* (2013.01); *A61B 5/6819* (2013.01);
(Continued)

(58) Field of Classification Search
None
See application file for complete search history.

(56) References Cited

U.S. PATENT DOCUMENTS

| 6,516,213 B1 * | 2/2003 | Nevo ..................... A61B 5/06 600/410 |
| 7,920,911 B2 * | 4/2011 | Hoshino .............. G01R 33/287 600/423 |

FOREIGN PATENT DOCUMENTS

| EP | 0964261 A2 | 12/1999 |
| ES | 2354939 T3 | 3/2011 |

OTHER PUBLICATIONS

Adam M.J. van Niekerk, et al., "Hybrid Motion Sensing with a Wireless Device, Self-Synchronized to the Imaging Pulse Sequence," Proceedings of the International Society for Magnetic Resonance in Medicine, ISMRM, Joint Annual Meeting, Paris, France, Jun. 16-21, 2018 (6 pages).
(Continued)

*Primary Examiner* — Katherine L Fernandez
(74) *Attorney, Agent, or Firm* — McCarter & English, LLP

(57) ABSTRACT

A wireless radio frequency triggered signal acquisition device includes three orthogonal pick up coils in which voltages will be induced by a time varying, spatially varying magnetic field inside a chamber of an MRI scanner. A radio frequency detection circuit detects radio frequency pulses emitted by an MRI scanner and a wireless transmission circuit transmits data from the device. A 3-axis magnetometer is used for measuring magnetic flux in the chamber of the MRI scanner. A processor uses the detected radio frequency pulses to synchronize measurements taken by the magnetometer and pickup coils to a time frame of a gradient driver hardware, thereby matching the measurements to a pulse sequence waveform. The processor further combines
(Continued)

measurements of induced voltages in the orthogonal pick up coils and the magnetic flux with the pulse sequence waveform in order to solve for the instantaneous position and orientation of the device.

10 Claims, 9 Drawing Sheets

(51) Int. Cl.
    *A61B 5/06*     (2006.01)
    *G01R 33/02*     (2006.01)
    *G01R 33/07*     (2006.01)
    *G01R 33/36*     (2006.01)
    *G01R 33/565*     (2006.01)
    *H01Q 1/27*     (2006.01)
    *H01Q 7/00*     (2006.01)

(52) U.S. Cl.
    CPC ....... *G01R 33/0206* (2013.01); *G01R 33/072* (2013.01); *G01R 33/3692* (2013.01); *G01R 33/56509* (2013.01); *H01Q 1/273* (2013.01); *H01Q 7/00* (2013.01)

(56) References Cited

OTHER PUBLICATIONS

ISMR—2018 Call for Abstracts, Sep. 11, 2017, https://www.ismrm.org/18m/2018-call-for-abstracts/ (6 pages).
A.J. van der Kouwe, et al., "Real-Time Prospective Rigid-Body Motion Correction with the EndoScout Gradient-Based Tracking System," Proceedings of the International Society for Magnetic Resonance in Medicine, ISMRM, 17th Scientific Meeting and Exhibition, Honolulu, Hawaii, Apr. 18-24, 2009 (1 page).
Adam van Niekerk, et al., "A Wireless Radio Frequency Triggered Acquisition Device (WRAD) for Self-Synchronised Measurements of the Rate of Change of the MRI Gradient Vector Field for Motion Tracking," IEEE Transactions on Medical Imaging, vol. 38, No. 7, Jul. 2019 (12 pages).
International Search Report of the International Searching Authority mailed on Oct. 21, 2019, issued in connection with International Application No. PCT/IB2019/054675 (4 pages).
Written Opinion of the International Searching Authority mailed on Oct. 21, 2019, issued in connection with International Application No. PCT/IB2019/054675 (9 pages).
Combined Search and Examination Report dated Dec. 18, 2018, issued by the United Kingdom Patent Office in connection with United Kingdom Application No. GB1809866.5 (5 pages).

\* cited by examiner

WIRELESS RADIO FREQUENCY TRIGGERED SIGNAL ACQUISITION DEVICE

RELATED APPLICATIONS

This application is a U.S. National Phase Application under 35 U.S.C. 371 of International Application No. PCT/IB2019/054675 filed Jun. 5, 2019, which claims the benefit of Great Britain Patent Application No. 1809866.5 filed on Jun. 15, 2018. The disclosures of these applications are incorporated herein by reference in their entireties.

BACKGROUND OF THE INVENTION

The present invention relates to a wireless radio frequency triggered signal acquisition device, particularly for use within a magnetic resonance imaging (MRI) scanner.

MRI scanners are most frequently used in medical environments to scan patients and also to scan objects located inside the scanner.

Over the past decade MRI scanner hardware has improved dramatically, however scan durations remain relatively long. This is because with improved scanner performance, clinicians rather opt to capture higher resolution images than reduce scan time. With sub-mm image resolution now possible, motion associated blurring and/or ghosting of the images can be caused by involuntary motion, such as the motion relating to cushion recovery as the patient relaxes. One can therefore appreciate that tracking and correcting of motion is of great interest as it not only prevents corruption of images caused by bulk motion, swallowing or discomfort (making them undiagnostic), but removes artefacts related to involuntary motion in all patients, including those who traditionally wouldn't have been considered moving.

Many techniques have been described to correct for motion, and one of these is disclosed in U.S. Pat. No. 6,516,213. This patent discloses applying a sensor to the object being monitored. The sensor described is comprised of three orthogonal pick up coils.

However, simply knowing the voltage vector measurements of the orthogonal pick up coils will not give enough information to determine the position and orientation of the device, a further piece of information is required to determine a reference frame in which the device is located.

This US '213 patent addresses this by using magnetic field maps of the gradient coils. These gradient field maps are however vulnerable to a variety of external factors such as the MRI hardware state, the waveform shapes used to acquire the map and human errors associated with how well the calibration procedure was carried out.

The present invention provides an alternative solution whereby systems of the kind disclosed in U.S. Pat. No. 6,516,213 can be implemented without the need for gradient field maps.

SUMMARY OF THE INVENTION

According to one example embodiment a wireless radio frequency triggered signal acquisition device includes:
   three orthogonal pick up coils in which voltages will be induced by a time varying, spatially varying magnetic field inside a chamber of an MRI scanner;
   a radio frequency detection circuit for detecting radio frequency pulses emitted by a Magnetic Resonance Imaging (MRI) scanner;
   a wireless transmission circuit for transmitting data from the device;
   a 3-axis magnetometer for measuring magnetic flux in the chamber of the MRI scanner; and
   a processor connected to the radio frequency detection circuit, pick up coils, wireless transmission circuit, and 3-axis magnetometer, the processor:
   using the detected radio frequency pulses to synchronize measurements taken by the magnetometer and pickup coils to a time frame of a gradient driver hardware, thereby matching the measurements to a pulse sequence waveform; and
   combining measurements of induced voltages in the orthogonal pick up coils and the magnetic flux with the pulse sequence waveform in order to solve for the instantaneous position and orientation of the device within the imaging volume of the MRI scanner.

The processor may further control the wireless transmission circuit to transmit data to an external processor regarding the position and orientation of the device inside the scanner.

The device additionally includes a memory for storing data.

In one example, the device further includes a dipole antenna shaped to saddle the bridge of a patient's nose and the processor, the radio frequency detection circuit, pick up coils, wireless transmission circuit and 3-axis magnetometer are connected to a main printed circuit board which will lie close to the sagittal plane of the body and allow maximum flux for the 2D radio frequency detection when the device is located on the nose of the patient.

According to another example embodiment a wireless radio frequency triggered signal acquisition method is provided, the method including:
   detecting radio frequency pulses emitted by a Magnetic Resonance Imaging (MRI) scanner using a radio frequency detection circuit for detecting radio frequency pulses;
   using three orthogonal pick up coils to detect a time varying, spatially varying magnetic field inside a chamber of an MRI scanner;
   measuring magnetic flux in the chamber of the MRI scanner using a 3-axis magnetometer;
   using the detected radio frequency pulses to synchronize measurements taken by the magnetometer and pickup coils to a time frame of a gradient driver hardware, thereby matching the measurements to a pulse sequence waveform; and
   combining measurements of the induced voltages in the orthogonal pick up coils and the magnetic flux with the pulse sequence waveform in order to solve for the instantaneous position and orientation of the device within the imaging volume of the MRI scanner.

Data may be transmitted from the device to an external processor.

In one embodiment the solving for the instantaneous position and orientation of the device is done by a processor of the device.

In another example embodiment the solving for the instantaneous position and orientation of the device is done by the external processor.

DESCRIPTION OF EMBODIMENTS

An MR image is formed by super-imposing spatially varying gradient fields onto a much stronger (generally 1,000-10,000 times) static magnetic field. The component of the gradient magnetic field parallel to the static magnetic field is well defined because this portion of the gradient field has a much stronger influence on the amplitude of the sum of the two magnetic fields.

It is often (almost always) desirable to produce a gradient magnetic field which, once superimposed on the static magnetic field, results in a linear change in field amplitude with respect to displacement in a principle direction. MRI scanners are usually constructed from 3 gradient coils, each producing a varying magnetic field in a mutually orthogonal direction. In this way, the 3 gradients form a basis set for 3 space (this can be referred to as the gradient coordinate frame).

A linear combination of the gradients can therefore be used to create a spatially varying magnetic field in any direction within the imaging volume of the MRI scanner.

Modifying the magnitude of a vector is most efficiently achieved by adding another vector which is parallel to the original vector. The highest efficiency would be to produce a gradient field which varies as previously discussed which is perfectly aligned to the static magnetic field, however no such field exists. It is a well-known fact that gradient coils that produce the linear encoding described need to produce coupled fields orthogonal to the static magnetic field in order to satisfy Maxwell's equations.

Although the orthogonal gradient fields have negligible influence on the amplitude of the magnetic field (often referred to as the gradient concomitant fields) within the scanner, their effect is easily observed in the time derivative of the gradient pulse waveform. The rate of change of magnetic flux can be measured with a pickup coil (through induction).

It is possible to construct a sensor comprised of 3 orthogonally mounted pickup coils to measure the change in flux vector. The orthogonally mounted coils define the basis set of the sensor measurement frame. One example of such a device is described in U.S. Pat. No. 6,516,213.

In this patent, the transform between the pickup coil sensor frame and the gradient coordinate frame is linked by a gradient field map which has the problems described in the background section above.

Figure 1:
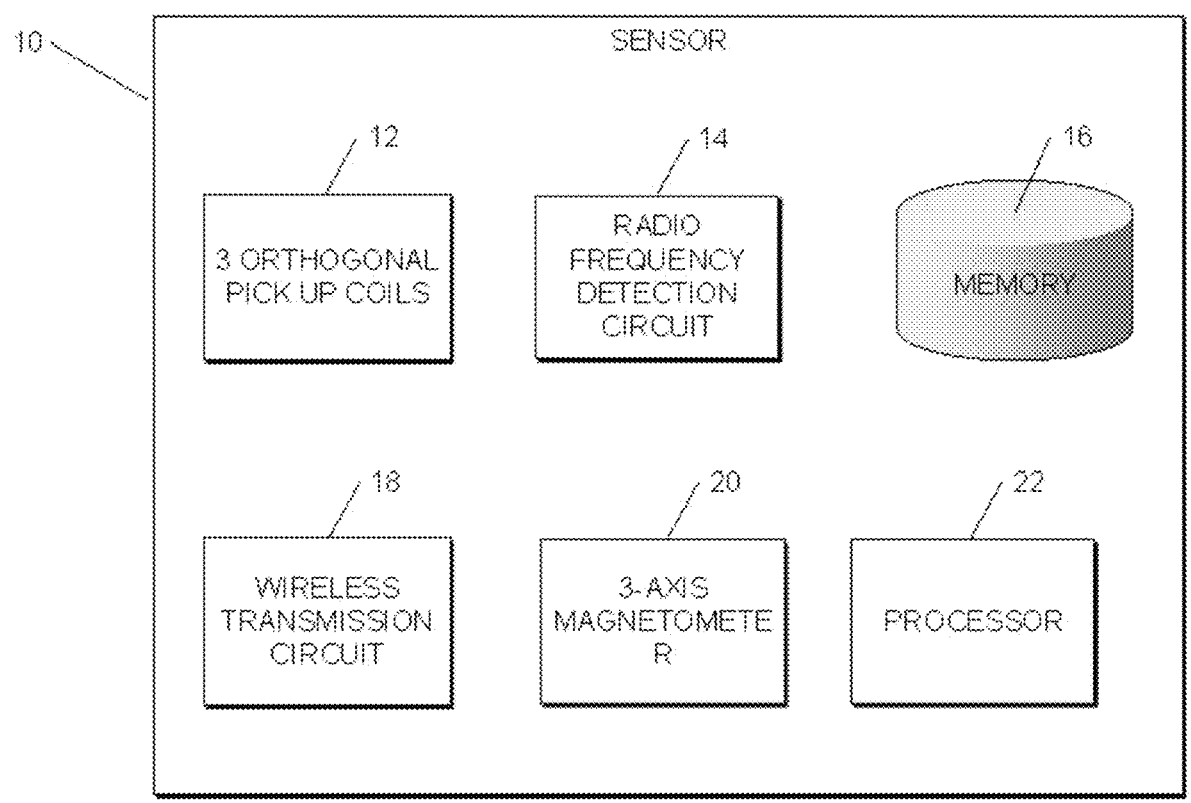
FIG. 1 is a block diagram illustrating an example wireless radio frequency triggered signal acquisition device according to the present invention.

Referring to FIG. 1, a wireless radio frequency triggered signal acquisition device 10 is illustrated.

The device in use will typically be placed on a patient inside a chamber of an MRI scanner as has been described above.

The device 10 includes three orthogonal pick up coils 12 in which voltages will be induced by a time varying, spatially varying magnetic field inside the chamber of the MRI scanner.

A radio frequency detection circuit 14 is used for detecting radio frequency pulses emitted by a Magnetic Resonance Imaging (MRI).

Memory 16 is used to store data.

A wireless transmission circuit 18 is used for transmitting data from the device.

3-axis magnetometer 20 is used for measuring magnetic flux in the chamber of the MRI scanner. The 3-axis magnetometer 20 (magnetic flux measurement device) measures the magnitude and direction of the magnetic field with respect to the coordinate frame of the magnetometer.

Processor 22 is connected to the pick up coils 12, radio frequency detection circuit 14, wireless transmission circuit 18 and 3-axis magnetometer 20 to control the operation of the device 10.

The processor 10 uses the detected radio frequency pulses to synchronize measurements taken by the magnetometer 20 and pickup coil assembly 12 to the time frame of the gradient driver hardware on the MRI scanner, thereby matching the measurements to a pulse sequence waveform.

It will be appreciated that other methods of synchronization could be used in addition to or as an alternative to the method described herein.

The processor 10 combines the measurements of the induced voltages in the orthogonal pick up coils 12 and the magnetic flux measurement from the magnetometer 20 with the pulse sequence waveform in order to solve for the instantaneous position and orientation of the device 10 within the imaging volume of the MRI scanner.

This is achieved as follows, the magnetometer 20 is rigidly attached to the 3 orthogonal pick up coil sensor 12 so the transform between the two sensor frames is constant and known.

The magnetometer 20 effectively measures the direction of the static magnetic field in the MRI chamber.

This can be used to solve for the portion of the measured voltage vectors in the pick up coils which lie parallel to the static magnetic field. Independent of the sensor frame orientation.

The gradient magnetic field encoding in this direction is considered known as without this knowledge interpretation of the MR signal data for image formation is not possible, thus enabling immediate interpretation of the position of the sensor frame with respect to the gradient coordinate frame in the direction of the current time varying gradient excitation.

The orientation of the pick up coil 12 sensor frame is almost fully constrained by the magnetometer measurement. The only degree of freedom unknown is about the axis of the static magnetic field. One can appreciate that with the location of the sensor frame known solving for the expected direction of the voltage vectors is greatly reduced.

For a typical MRI scanner hardware setup, with a cylindrical layout so that the patient can be comfortably placed in a supine position, the off axial gradient encoding is almost always achieved using coils wound in what is called a Golay configuration. These coils possess the unique property in that the vectors they produce lie on a plane. This allows for a closed form solution to the orientation of the sensor frame because these gradients produce a vector orthogonal to the static magnetic field proportional to displacement in the axial direction.

The methodology will now be described in more detail.

As mentioned above, the rate of change of the gradient magnetic waveforms with respect to time within the scanner are of interest.

The temporally stationary static magnetic field within the scanner falls away making the concomitant (orthogonal to the static magnetic field) and conventional gradient magnetic fields equally visible.

The slew is therefore a vector quantity which encodes the MRI scanner imaging volume in more than one spatial direction at a time with a single gradient excitation.

Theoretically this means that the magnetic vectors more efficiently encode position than any frequency based technique which resolves the gradient fields into a scalar quantity. This information is useful when tracking subject motion as position and orientation estimates are possible using, for example, a sensor comprised of 3 orthogonal pick up coils 12.

The present invention provides that by combining the gradient vectors measured by the 3 orthogonal pick up coils with a vector observation of the direction of the static magnetic field, a closed form solution to displacement and orientation in the gradient co-ordinate frame is provided.

The voltage induced across the 3D pickup coil 12 (which is relatively simple to construct) relates to the rate of the gradient waveforms at that instant in time. The hardware used to digitise the pickup potential effectively introduces new analogue to digital (ADC) sampling events defined in the pulse sequence time frame.

Preferably the signal acquisition windows are kept very short (<1 ms) to minimise any influence on the parent (imaging) pulse sequence timing. The device 10 is therefore required to be precisely synchronised to the imaging pulse sequence to allow correct interpretation measured voltage vectors.

For this purpose most modern MRI scanners have optical synchronisation capabilities allowing external events to be triggered at precise intervals as specified by the pulse sequence programmer. However, when introducing external hardware, which requires physical connections to the MRI scanner, new challenges arise which can affect the imaging workflow.

It will be appreciated that with the device 10 of the present invention, the use of a synchronisation signal from the scanner control computer and the associated cabling is avoided.

Instead the radio frequency detection circuit 14 detects the radio frequency (RF) pulses of the parent pulse sequence which are then used as synchronisation events.

The advantage of using RF pulses lies in the ease of portability between different imaging pulse sequences as the RF pulses conveniently define the contrast of the acquisition.

The radio frequency detection circuit 14 detects RF pulses using a wireless resonant marker tuned to the precession frequency of the MRI scanner.

A passive detuning circuit is modified to charge a tank capacitor while maintaining effective detuning.

In order to communicate the data acquired by the device 10 out of the scanner, a 2.4 GHz radio link circuit 18 was developed.

Real-time data visualisation of the acquired signals is possible with short high data-rate packet transfers, avoiding overlap with critical sections of the parent pulse sequence (during sampling of the MR signal).

In a prototype embodiment, in order to validate the method, sinusoidal gradient play-outs were introduced into the imaging pulse sequence. The potential induced in a 3D printed circuit board (PCB) pickup coil is filtered, amplified, sampled (using a 12-bit ADC) and analysed in real-time using the device's on-board controller 22.

To evaluate the efficacy of the method a 3D spoiled gradient echo pulse sequence is modified to play out 3 sinusoidal pulses, one in each of the gradient axes.

The deviation of the phase of the sinusoidal potential induced across the pickup coil on the device 10 and the gradient waveform played out in the pulse sequence time domain are compared to allow real-time measurement of timing offsets between the device 10 and pulse sequence time frames.

Once accurate synchronisation is achieved the relationship between position in the gradient co-ordinate frame and the slew vector is examined.

Figure 2:
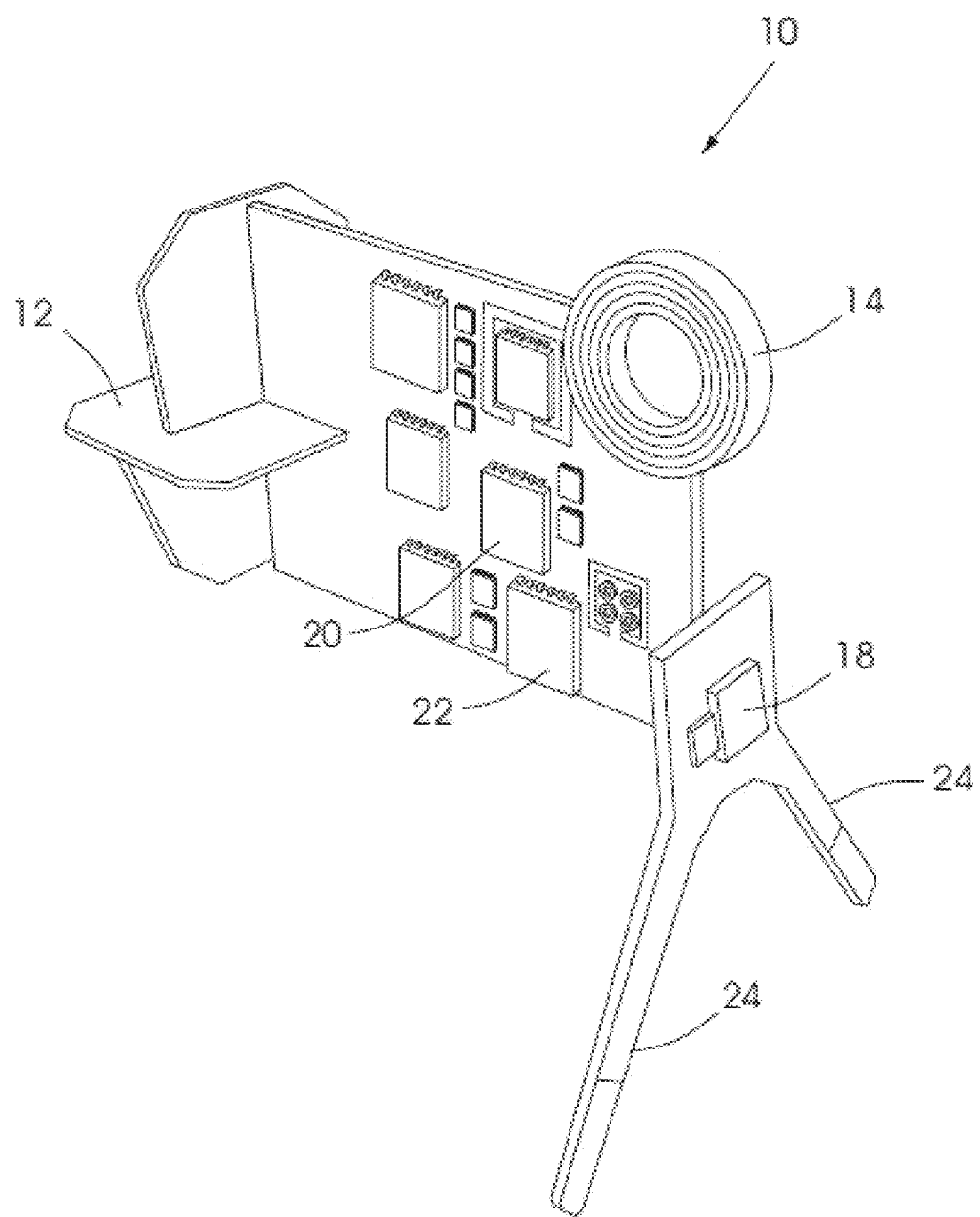
FIG. 2 is a schematic illustration of the device of FIG. 1.

The prototype of the present invention was designed using a 2.4 GHZ dipole antenna 24 shaped to saddle the bridge of the subject's nose. This can be seen in FIG. 2.

The main printed circuit board (PCB) would therefore lie close to the sagittal plane of the body and allows maximum flux for the 2D RF detection antenna.

The processor 22 in the form of a microcontroller unit (MCU) and the associated analogue circuitry are also on the sagittal plane to minimise cross sectional area relative to the nearest RF receiver elements.

The pickup coil 12 was constructed from 3 PCB fabricated inductors (Z axis on the main PCB, X and Y from separate PCBs) each precisely cut with slots to allow orthogonal mounting representing the principle axes of the device's 10 co-ordinate frame.

The device hardware of the prototype was designed and fabricated using standard electronic components, however care was taken in selecting packages that contain minimal nickel.

The pulse sequence was implemented on a 3 T Skyra MRI scanner (Siemens, Erlangen, Germany).

The device (FIG. 2) comprises the following main circuits:
  The RF detection circuit 14 for producing synchronisation pulses.
  An analogue amplification and filtering circuit for processing the pickup voltages before digitisation.
  The micro-controller 22 with built in 12-bit analog digital converter to sample the pickup coil potentials and do signal processing and digital communication with the magnetometer 20 and 2.4 GHz wireless transmission circuit 18.
  The wireless transmission circuit 18 to communicate results out of the MRI scanner.
  The 3-axis Hall Effect magnetometer 20 for measuring the direction of the static magnetic field.

The device was constructed using a 2-layer printed circuit board 0.6 mm thick, measuring 35 mm over its largest dimension.

Figure 3:
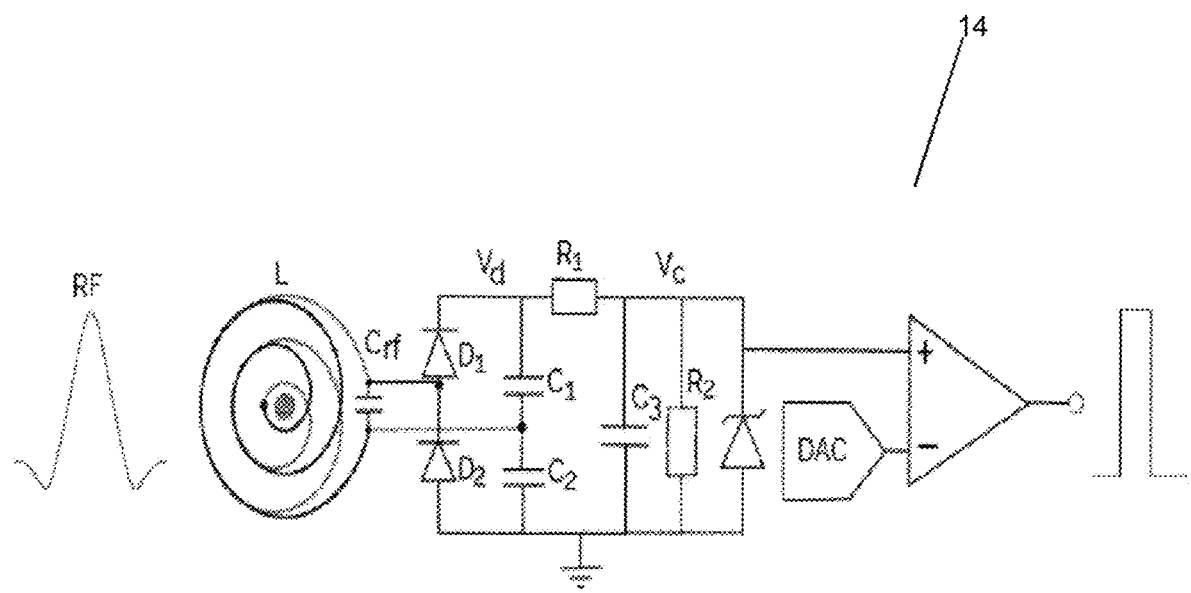
FIG. 3 is an example circuit diagram of the radio frequency detection circuit of FIG. 1.

An example circuit diagram of the RF detection circuit 14 used in the prototype is shown in FIG. 3.

A resonant marker comprised of a PCB inductor (L) and tuning capacitor (Crf) was constructed.

The resonant circuit was tuned using a circular loop connected to handheld antenna analyser.

A sample (red dot) was constructed from a glass sphere filled with polyethylene glycol (PEG). The high frequency RF signal is rectified using diodes D1 and D2 and charging capacitors C1 and C2 which are connected in series, doubling the peak-to-peak AC signal. This configuration is commonly known as a Delon Doubler.

The doubled potential (Vd) then charges the tank capacitor C3 through R1.

As the diodes become more conductive the capacitance changes, detuning the resonant portion of the circuit.

R1 controls the charge current of the capacitor and forms a potential divider with R2.

The selection of R2 controls the discharge rate of C3 adjusting the pulse width of the detection pulse.

A Zener diode protects the comparator in case the divided potential (Vc) exceeds the input threshold.

A high speed 12-bit digital to analog converter (DAC) is connected to the negative terminal of the comparator allowing real-time adjustment of the detection threshold. The comparator is built into the microcontroller and has a programmable hysteresis level (15 mV) which, when combined with the low pass nature of the charge circuit, avoids any bouncing of the digital output signal.

Figure 4:
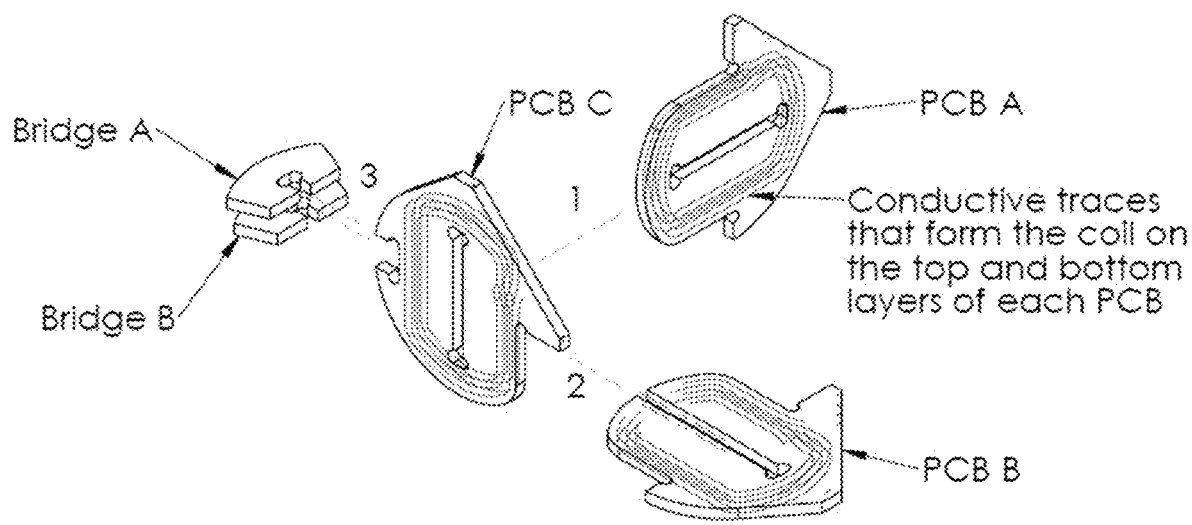
FIG. 4 is an example of the 3 orthogonal pick up coils circuit of FIG. 1.

An example configuration of the 3 orthogonal pick up coils 12 used in the prototype is shown in FIG. 4.

In this configuration, each pickup coil is formed on a printed circuit board (PCB) using conductive traces that form the coil on the top and bottom layers of each PCB.

Three pickup coils are formed in this manner as illustrated and assembled by PCB A sliding into PCB C. PCB B then slides into the assembly of PCBs A and B.

Bridge A and Bridge B connect the conductive traces in PCB B.

Figure 5:
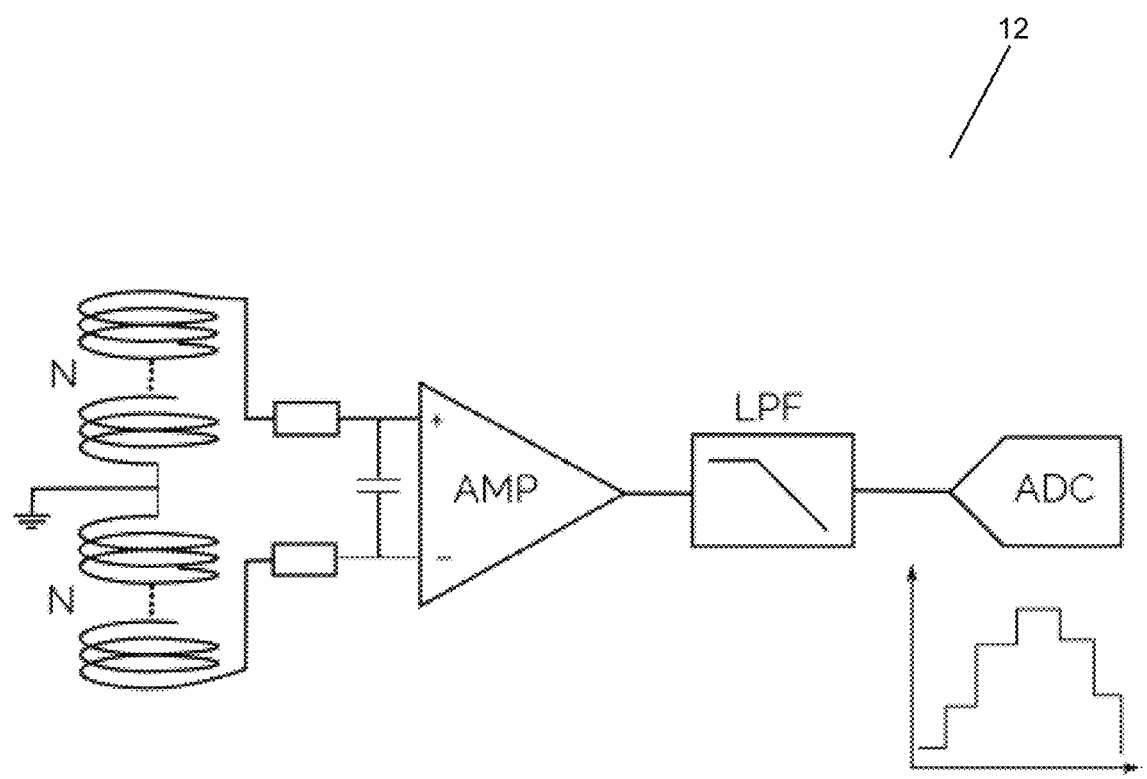
FIG. 5 is an example circuit diagram of the 3 orthogonal pick up coils circuit of FIG. 1.

An example circuit diagram of the 3 orthogonal pick up coils 12 used in the prototype is shown in FIG. 5.

Each pickup coil circuit was designed with 18 turns, 9 (N) on each side of the PCB.

An active analogue low pass filter (LPF, 3 pole Butterworth) with a cut-off frequency of 16 kHz is applied to the signal before sampling at 200 KHz.

The device 10 ADC sample frequency was chosen to align to the gradient raster timing of the scanner.

Two ADC samples on the device 10 to one time step in the MRI scanner's gradient raster time (10 µs, for the prototype system) frame.

The first pole placed before the instrumentation amplifier (AMP) is used to eliminate any high frequency signals, such as RF, before amplification.

The instrumentation amplifier had a programmable gain setting (k) of 1-128 in powers of 2.

The design described above uses 3 orthogonal planar pickup coils, each measuring the magnitude of the flux normal to its surface (x, y, z). These combined to form a 3D slew sensor. The electric field (e) induced in a conductor with a time varying field can be described as:

$$\oint_{\partial \Sigma} e \cdot d\ell = -\frac{d}{dt} \int \int_{\Sigma} (b + B_0 z) \cdot da,$$

which for the case of a planar conductor with unit normal n, which is wound in a left handed fashion, results in the induced voltage:

$$v = -a\left(Sp \cdot n + [b(p) + B_0 z] \cdot \frac{\partial n}{\partial t}\right),$$

where α is a constant scaling factor which relates to the geometric properties of the pickup coil and incorporates the instrumentation amplifier gain (k). The second term is as a result of angular rate of change of the pickup coil in the static magnetic field:

$$\frac{\partial n|}{\partial t} = [\omega] \times n$$

w is the angular rate of change in the scanner frame and the [·]x operator converts a vector into a 3 by 3 skew matrix representing the vector cross product.

In this case the static magnetic field is not negligible and the induced voltage could affect results, however the gradient pulses used to induce potential generally last less than 1 ms. The expected change in angular rate of change over such a short period is expected to be negligible, therefore this term can be treated as a small constant offset which can be eliminated or separated for measurement; if a useful 2 axis angular rate sensor is desired.

Figure 6:
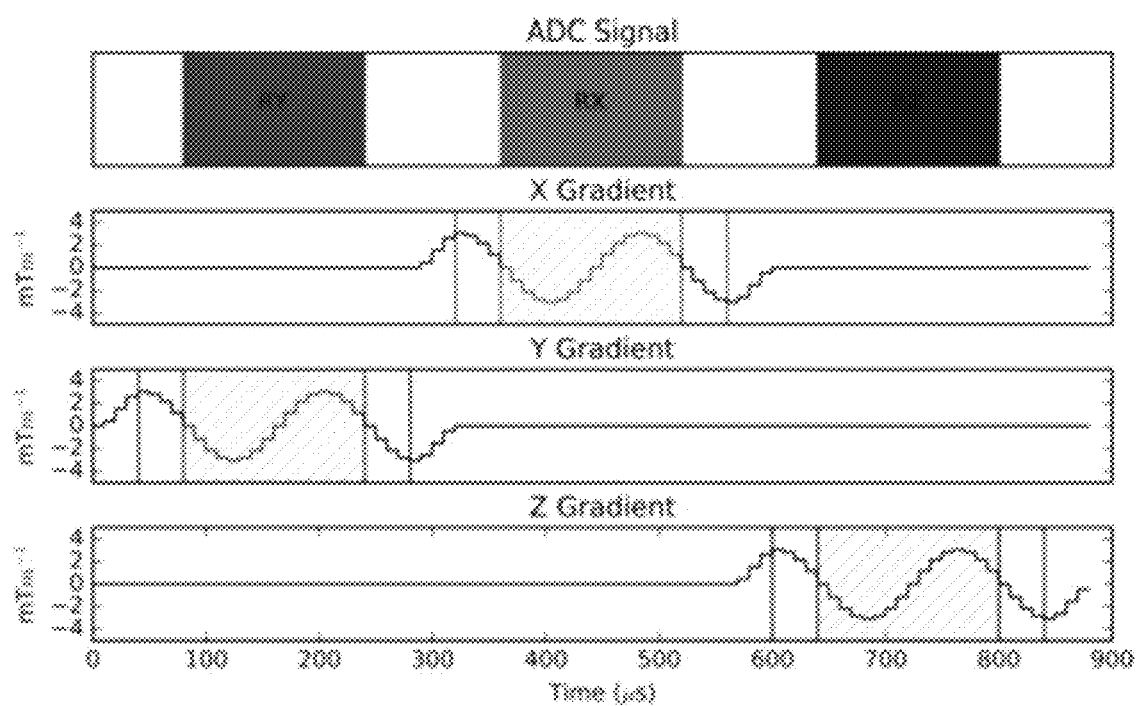
FIG. 6 shows a pulse sequence with sinusoidal waveforms played out in each gradient axis which was designed for the pickup coil excitation.

A pulse sequence with sinusoidal waveforms played out in each gradient axis was designed for the pickup coil excitation. This is illustrated in FIG. 6 which shows a sinusoidal gradient waveforms lasting a total of 880 us with highlighted ADC acquisition windows.

The hatched regions show the desired ADC timing where the outer bounded regions show the maximum allowable timing offset in which the waveforms remain sinusoidal, effectively forming a buffer for any offset between the device and the gradient time frames.

With a gradient raster timing of 10 µs, the portion of the gradient excitation to be sampled by the device 10 has a duration of 16 samples per revolution (160 µs at 6.25 kHz) ensuring perfect symmetry of the discrete waveform with 4 samples for each quarter rotation.

An extra quarter rotation before and after each readout window (RX, RY, RZ) ensures the waveform remains sinusoidal if there is an offset between the device sample time and the MRI scanner gradient raster time (40 µs).

The initial and final ramp (quarter rotation) of each waveform is implemented using a shifted cosine function at double the frequency and half the amplitude, to maintain the designed slew rate of the measured excitation. This ensures that the time derivative of the gradient play-out is smooth, allowing for a linear response from the analogue filter. The results presented were obtained with a peak slew rate of 60 T/m/s with each readout lasting a total of 240 µs. All parameters of the waveform are implemented to be user adjustable along with the protocol of the parent pulse sequence.

The MRI scanner used for the results presented (a typical clinical MRI scanner layout) is constructed using 2 Golay coils, one orientated to produce a magnetic field which varies in the direction of the static magnetic field proportional to displacement in the x direction (x gradient) and the other rotated 90 degrees about the static magnetic field to produce an identical spatially varying field in the y direction (y gradient). The z gradient is produced by a Maxwell/Heimholtz coil pair axially aligned to the static magnetic field. By assuming the gradients produce linear spatial encoding and then constraining Maxwell's equations by assuming negligible change in curl and divergence with respect to time, the rate of change of magnetic flux within the imaging volume can be written in the following form:

$$s = Sp = \begin{pmatrix} -\frac{s^{g_z}}{2} & 0 & s^{g_x} \\ 0 & -\frac{s^{g_z}}{2} & s^{g_y} \\ s^{g_x} & s^{g_y} & s^{g_z} \end{pmatrix} \begin{pmatrix} x \\ y \\ z \end{pmatrix}$$

$s^{gz}$, $s^{gx}$, $s^{gy}$ are the rate of change of the x, y and z gradients respectively. x, y, z represent the position in the gradient coordinate frame.

Based on the above equation it can be seen that the 3 gradients uniquely encoding the imaging volume. This can be re-written in the following form:

$$f^{XZ} = \frac{s^{g_x}}{s^{g_x}} = \begin{pmatrix} z \\ 0 \\ x \end{pmatrix}, f^{YZ} = \frac{s^{g_y}}{s^{g_y}} = \begin{pmatrix} 0 \\ z \\ y \end{pmatrix} \text{ and } f^{Zxy} = \frac{s^{g_z}}{s^{g_z}} = \begin{pmatrix} -\frac{x}{2} \\ -\frac{y}{2} \\ z \end{pmatrix}.$$

Therefore based on the previously described gradient waveforms the MRI scanner produces a spatially varying slew vector (f) scaled by the time derivative of the gradient waveform shape (FIG. 6) S(t):

$S(t) = -S \cos(wt)$ where S is the maximum slew rate of the gradient pulse. Each pickup coil of the device observes the slew as a voltage in mutually orthogonal directions which can be combined to form a voltage vector:

$W_v = \alpha S \cos(wt+\theta) W_f$ where α is a constant scaling factor relating to the cross sectional area of the pickup coils, number of turns and gain of the amplifier circuit, the leading superscript ($^w\cdot$) denotes the device observation frame and θ models timing offsets between the DEVICE Time frame and the gradient time frame (this was used to validate the RF detection circuit precision and accuracy). The spatial slew encoding vector (f) could be any linear combination of the terms ($f^{XZ}$, $f^{YZ}$, $f^{Zxy}$) rotated into the device reference frame. In the pulse sequence design presented only one gradient is excited at a time.

The 12-bit ADC samples the potential across each of the three pickup coils for the entire duration of the sinusoidal play-outs discarding the data acquired between the desired acquisition windows.

The micro-controller treats the data in quarter rotations ($N_q = 4 N_{GRT} = 8 N_{WRAD}$) in a similar fashion to the pulse sequence design. A Goertzel filter is applied to the data in each readout window which isolates the frequency component of the designed waveform ($2\pi/4Nq$). Each filter step is computed on a per sample basis (once every 5 μs) as the pickup potential is sampled. The result is therefore ready for transmission within 5 μs of the last sample of the final readout (RZ). The Goertzel filter is a single bin discrete Fourier transform (DFT) computing the phase and amplitude of the tone measured by the pickup coil. Applying the Goertzel filter to the induced potential and scaling the result from the proposed pulse sequence waveform shape one obtains the following complex vector:

$$\frac{w_v}{\alpha S} \xrightarrow{\mathcal{F}_w} {^w_c}r = \begin{pmatrix} w_{f_x} e^{i\theta_x} \\ w_{f_y} e^{i\theta_y} \\ w_{f_z} e^{i\theta_z} \end{pmatrix}$$

To interpret the values obtained from the Goertzel filter the spatial encoding vector is first recovered:

$w_{f_i} = \mathrm{abs}(^W_c r_i) \mathrm{csgn}(^W_c r_i)$ for $i = [x, y, z]$, where $\mathrm{abs}(\cdot)$ is the magnitude of the complex vector and $\mathrm{csgn}(\cdot)$ is the sign of the real component of the complex vector.

The 3 readouts RY, RX and RZ produce the following system of equations:

$$^W f^{RX} = {^W_G}R \begin{pmatrix} z \\ 0 \\ x \end{pmatrix}, \; ^W f^{RY} = {^W_G}R \begin{pmatrix} 0 \\ z \\ x \end{pmatrix}, \; ^W f^{RZ} = {^W_G}R \begin{pmatrix} -\frac{x}{2} \\ -\frac{y}{2} \\ z \end{pmatrix}$$

Where $^W_G R$ is a rotation matrix, which transforms a vector from the leading subscript frame to the leading superscript frame.

The 3 axis hall effect magnetometer 20 measures the direction of the static magnetic field in the device coordinate frame, which when normalised can be interpreted as the principle z-axis of the gradient frame:

$$\frac{W_m}{B_0} = w_{\bar{z}} = {^W_G}R^G \bar{z}$$

Obtaining the x and y axes in the device frame can then be achieved by using the x gradient readout:

$$W_{\bar{y}} = \frac{[W_{\bar{z}}] \times W_f RX}{\|W_f RX\|}, \; W_{\bar{x}} = [W_{\bar{y}}] \times W_{\bar{z}}$$

or the y gradient readout:

$$W_{\bar{x}} = \frac{[W_f RY] \times W_{\bar{z}}}{\|W_f RY\|}, \; W_{\bar{y}} = [W_{\bar{z}}] \times W_{\bar{x}}.$$

Each of which can be used to form the rotation matrix:

$$^W_G R = [W_{\bar{x}} \; W_{\bar{y}} \; W_{\bar{z}}],$$

which can be used to obtain the position of the device in the gradient coordinate frame ($^G_W R = {^W_G}R^T$):

$$\begin{pmatrix} z \\ 0 \\ x \end{pmatrix} = {^G_W}R \, ^W f^{RX}, \; \begin{pmatrix} 0 \\ z \\ x \end{pmatrix} = {^G_W}R \, ^W f^{RY}, \; \begin{pmatrix} -\frac{x}{2} \\ -\frac{y}{2} \\ z \end{pmatrix} = {^G_W}R \, ^W f^{RZ}$$

No RF shielding of any of the electronics was implemented in the prototype as conductive planes interact with the gradients causing high frequency vibration. This could be unpleasant when mounted on a patient's head.

This affected the design of the 2.4 GHz antenna, where a ground plane for a monopole antenna wasn't practical. A V-shaped dipole antenna was therefore designed to fit the form factor of the bridge of the subject's nose.

Due to the strict timing requirements of data transmissions, a proprietary RF protocol (Enhanced Shockburst, Nordic Semiconductor) was implemented, enabling low latency bidirectional communication between the device and a laptop situated in the scanner control room.

The sinusoidal play-outs are inserted before the parent sequence readout. The readouts with very short echo times allow for a strong MR signal to capture using the MRI scanner's ADC and compare to the slew vector waveforms captured by the device ADC. The time between the start of the RF pulse and first readout ($t_0$) is of importance in setting the device RF trigger wait period.

The transfer window of 570 µs over the phase encode and pre-wind gradients is sufficiently long for a 32-byte payload transfer and 2-byte acknowledge over the 2.4 GHz radio link. The acknowledge payload for each packet sets the initial wait period $t_0$ and the number of samples in gradient raster timing (GRT) for each quarter rotation ($N_q$) of the sinusoidal pulse, effectively enabling real-time adaption of the pulse sequence parameters (delayed by one TR due to the way in which events are queued by the scanner software). For better pulse sequence co-existence short burst transmissions are preferable, therefore all signal analysis is done on the device in real-time and only the results are transmitted. For debugging purposes a verbose mode was also implemented to allow real-time visualisation of the excitation waveforms, gradient timing offsets, amplitudes and magnetometer measurements; requiring the transmission of 7 Packets for each line of k-space.

Implementing the above it was found that without any modifications/connections to the scanner hardware the prototype device 10 could be used to visualise short snippets of the gradient flux from a variety of different pulse sequences.

By implementing a simple plotting program which takes advantage of the bidirectional communication link it is possible to control the acquisition window for repetitive pulse sequences and plot the raw data in an oscilloscope like fashion.

It was found that a voltage threshold of 100 mV reliably triggers ADC events on the device down to a flip angle of 12 degrees with a non-selective RF pulse. The ability to adjust detection threshold (sensitivity) allows reliable RF pulse detection over a large range of marker tuning frequencies ($f_0 \pm 10$ MHz) making this technique insensitive to drift in component values.

The device managed to achieve high SNR measurements of the gradient slew with exceptionally stable timing.

The Goertzel filter effectively separated the sources of deviations present in the raw waveforms with stable amplitude and phase delay measurements. Once within the readout window, the delay estimates from the Goertzel filter are very stable, precisely tracking the trigger delay adjustments as they are stepped in 1 µs increments. The efficacy of the RF detection circuit could therefore be verified with sub-microsecond precision.

The change in phase and magnitude of the digitised signals relative to their means indicated robust estimates of both properties. The periodic spiking fluctuations which were observed are well correlated to the phase encoding of the parent pulse sequence.

At a trigger period of $t_{offset}$ (4 µs) shorter than the actual pulse sequence timing (to) the device measures a 0 µs phase shift of the pickup potential. This corresponds to the phase delay caused by the analog filter which was expected to be 6 µs by design, however passive component tolerances could have influenced the final implementation. This timing offset represents a constant shift which needs to be considered when interpreting the instantaneous rate of change of the gradient magnetic field Slight imperfections in the waveforms were found which are consistent even when the trigger period is adjusted to capture different portions of the waveform. Interestingly, they are also symmetric indicating that they are the result of small oscillations of the gradient waveform, having the form of an amplitude modulated signal. When considering the time scale of these acquisitions and that the shape is defined using 16 discrete points these artefacts could be expected.

To test the relationship between position and the slew vector described above, the prototype device was attached to a Lego block and displaced along the x, y and z directions in 8 mm increments.

Figure 7:
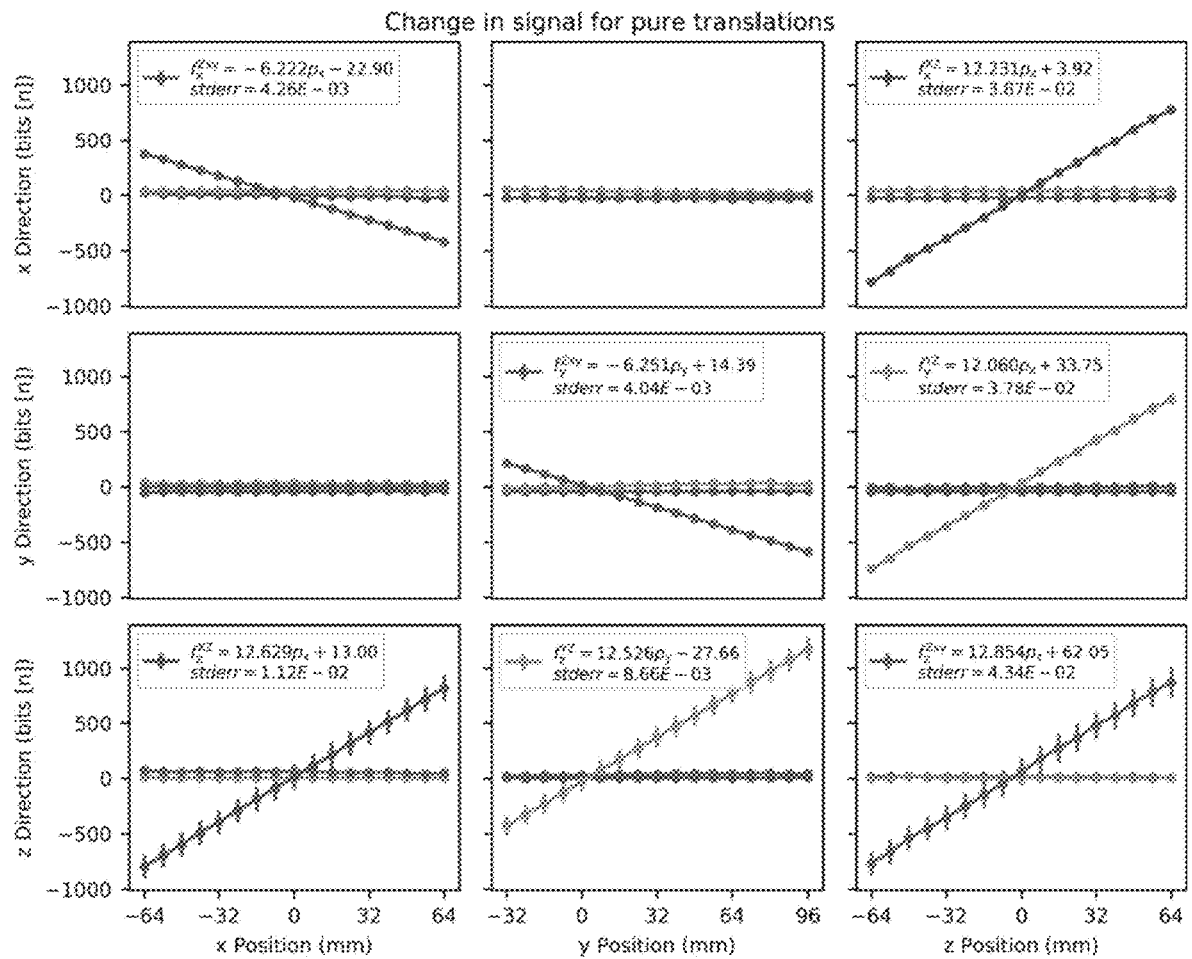
FIG. 7 shows the slew vector in the gradient coordinate frame of a prototype of the device during testing.

FIG. 7 shows the slew vector in the gradient coordinate frame. The device 10 (randomly oriented) independently displaced along the gradient x (column 1), y (column 2) and z (column 3) axes of the gradient coordinate frame. All error bars represent 100 standard deviations from the mean. The digitised readouts of the waveform from the x gradient producing the slew vector $f^{xz}$ are coloured in blue, the y gradient producing the slew vector $f^{yz}$ is coloured in orange and the z gradient producing the slew vector $f^{zxy}$ is coloured in green.

The device was shown to isolate the components of the flux vector using the magnetometer measurement even though it is randomly oriented. The direction of the slew vector from the x gradient ($f^{xz}$) and the magnetometer were used to resolve the slew vector from the y gradient ($f^{yz}$) into the gradient coordinate system using a rotation matrix described above.

Similarly, the direction of the slew vector from the y gradient and the magnetometer were used to resolve the slew vector from the x gradient using another rotation matrix described above.

By resolving the slew vectors in this way non-orthogonality of the flux vectors produced by the x and y gradients are purposefully projected into the measurements. These are most visible on the (row 2, column 1) and (row 1, column 2) shown in FIG. 7. The small (1%) correlation of the $f_y^{xz}$ and $f_x^{yz}$ terms with displacement in the x and y direction indicate that the flux for the x and y gradients are planar and very close to orthogonal. This can be expected as it is necessary for correct image formation. Variance in the direction of the slew vectors obtained from the x and y gradients is dependent on the magnitude of the z displacement.

It will be appreciated that the orientation is undefined for a z displacement of 0. For a typical z displacement of 30 mm the orientation of the device is stable to within 0.01 degrees about the z axis from the slew vector estimates, and 0.005 degrees about the orthogonal axes because the magnetometer estimate is exceptionally stable. A vector observation of the flux from the x and y gradients could be combined with an estimate of the direction of gravity from an accelerometer and smoothed for a more robust implementation (defined for all z). By applying the linear fits, position estimates accurate to within 0.2 mm are possible for displacement in all 3 directions.

Figure 8:
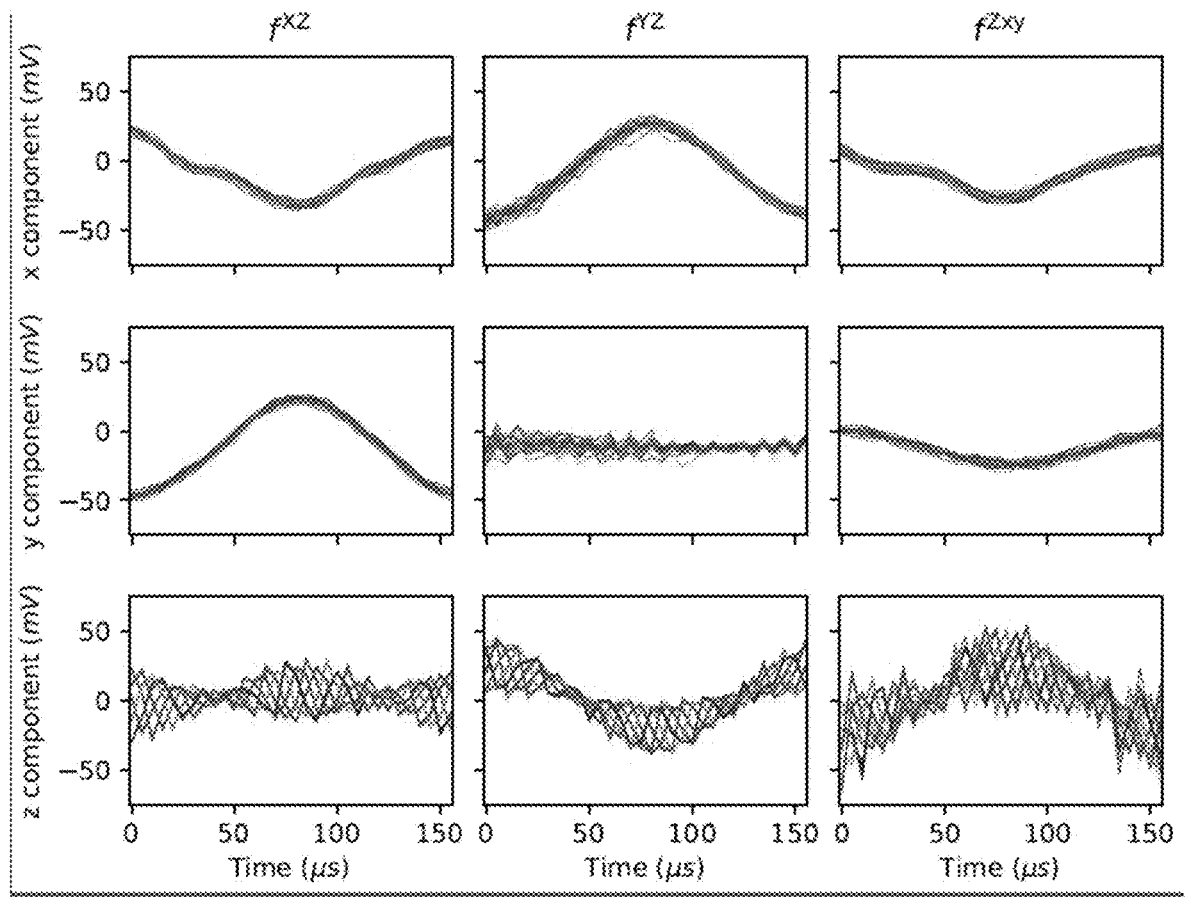
FIG. 8 shows an unexpected 40 KHz disturbance (caused by the switching of the gradient amplifier) measured by the prototype device. The figure shows how the disturbance is most prevalent in the direction of the static magnetic field (z-direction)

An increased variance in the slew vector waveforms parallel to the static magnetic field was measured (FIG. 7, bottom row). On closer inspection (FIG. 8) a 40 kHz disturbance is seen modulating the recorded gradient waveform. This can be explained by the switching frequency of the gradient amplifier which produces a pulse width modulated signal centred at 40 KHz.

It can thus be appreciated that with the present invention measurement variance can be more accurately accounted for because the gradient coils have directional coupling with each other and the superconducting electromagnetic which produces the static magnetic field. Due to the inclusion of the magnetometer (magnetic flux sensor) the present invention has been able to identify this unexpected ripple artefact in the slew vector waveform. The amplitude and frequency of the disturbance can be quantified by the device, allowing for its removal in subsequent measurements and a notable improvement in measurement precision to within 0.1 mm.

Figure 9:
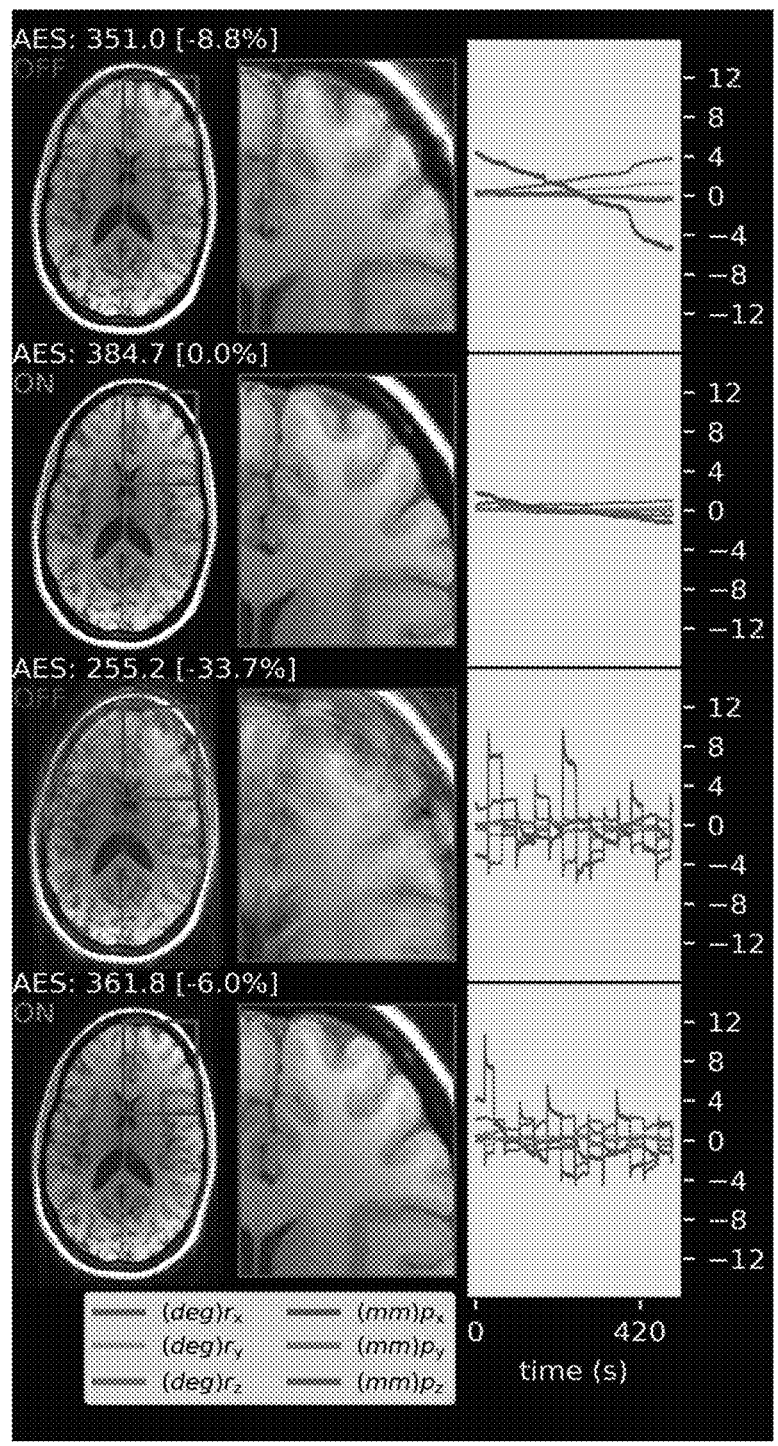
FIG. 9 shows some images taken with and without the device showing an improvement in image quality when the device is used.

Referring to FIG. 9, the efficacy of motion correction for deliberate motion is shown where in the top two rows of images the subject was asked to remain still. In the bottom two rows of images, the subject moved once every 20 seconds. The second and final row includes the use of the device with motion correction active. The clear improvement in image quality can be observed.

In summary it was found that the prototype of the device reliably and precisely tracked the gradient slew rate using a small 3D pickup coil. The conveniently small and plug and play nature of this device allows researchers to capture a variety of signals during MRI experiments.

Knowledge of the pulse sequence timing allows smarter co-existence of electronics with the MRI scanner enabling control of when data transmissions occur or powering down oscillators to avoiding overlap with ADC events. Smart sampling of high bandwidth sensors vulnerable to gradient pulses can be achieved during periods of gradient inactivity. This would be beneficial to combined MR-EEG/MR-ECG experiments. The use of the active marker as a signal source for high speed navigators is also possible, opening up sensor fusion strategies for more robust position estimates.

The 3D nature of the gradient slew encodes a wealth of information about the position and orientation of the device 10 within the gradient co-ordinate frame. The addition of a magnetometer allows a computationally efficient way of solving and interpreting the induced potentials.

The orthogonal components of the slew vector produced by the gradients are cleaner than the components parallel to the static magnetic field; likely due to coupling effects. Position can be encoded with a single pulse lasting only 240 μs from the z gradient, highlighting the efficiency of position encoding using the slew vector (solving for orientation would be more challenging in this case). The pulse sequence waveforms presented are short, however there is still room for optimisation. Due to the way in which the parallel and orthogonal components of the slew vector are interpreted any slight misalignment between the magnetometer and 3D pickup coil could result in the projection of biases into the position estimate, affecting accuracy. The large amount of data obtained from the 880 μs long excitation pulse series presented is well suited to sensor fusion techniques (eg. Kalman filter) where magnetometer biases could be tracked and corrected in real-time enabling the device to be used for prospective motion correction.

Accurate timing of the MRI scanner hardware is paramount to obtaining the k-space trajectories envisioned by the pulse sequence programmer. If any external hardware is introduced which modifies the way in which the gradient waveforms are played out (such as prospective motion correction) or a time sensitive signal which could affect the interpretation of the MR signal (such as a response to a stimulus in an fMRI experiment or PET MRI), it is important to maintain accurate synchronisation between the scanner and external data acquisition unit as the signal integrity can be degraded due to time frame misalignment. In this work we have managed to successfully design and implement a novel self-synchronising probe for use in the MR scanner which can interrogate gradient waveform timing.

The invention claimed is:

1. A wireless radio frequency triggered signal acquisition device including:
   three orthogonal pick up coils in which voltages will be induced by a time varying, spatially varying magnetic field inside a chamber of a Magnetic Resonance Imaging (MRI) scanner, wherein the three orthogonal pick up coils measure voltage vectors by sensing both a magnitude and direction of the time varying, spatially varying magnetic field;
   a radio frequency detection circuit for detecting radio frequency pulses emitted by the MRI scanner;
   a wireless transmission circuit for transmitting data from the device;
   a 3-axis magnetometer for measuring magnetic flux vectors of a static magnetic field in the chamber of the MRI scanner; and
   a processor connected to the radio frequency detection circuit, the three orthogonal pick up coils, the wireless transmission circuit, and the 3-axis magnetometer, the processor:
     using the detected radio frequency pulses to synchronize measurements taken by the 3-axis magnetometer and the three orthogonal pick up coils to a time frame of a gradient driver hardware, thereby matching the measurements to a pulse sequence waveform; and
     combining the voltage vectors measured by the three orthogonal pick up coils and the magnetic flux vectors of the static magnetic field with the pulse sequence waveform in order to solve for the instantaneous position and orientation of the device within an imaging volume of the MRI scanner.

2. The device of claim 1 wherein the processor further controls the wireless transmission circuit to transmit data to an external processor regarding the position and orientation of the device inside the scanner.

3. The device of claim 1 further including a memory for storing data.

4. The device of claim 1 wherein the device further includes a dipole antenna shaped and adapted to saddle the bridge of a patient's nose.

5. The device of claim 4 wherein the processor, the radio frequency detection circuit, the three orthogonal pick up coils, the wireless transmission circuit and the 3-axis magnetometer are connected to a main printed circuit board which will lie close to the sagittal plane of the patient's body and allow maximum flux for the 2D radio frequency detection when the device is adapted to be located on the nose of the patient.

6. A wireless radio frequency triggered signal acquisition method, the method including:
   detecting radio frequency pulses emitted by a Magnetic Resonance Imaging (MRI) scanner using a radio frequency detection circuit for detecting radio frequency pulses;
   using three orthogonal pick up coils to detect a time varying, spatially varying magnetic field inside a chamber of the MRI scanner, wherein the three orthogonal pick up coils measure voltage vectors by sensing both a magnitude and direction of the time varying, spatially varying magnetic field;

measuring magnetic flux vectors of a static magnetic field in the chamber of the MRI scanner using a 3-axis magnetometer, wherein a device includes the radio frequency detection circuit, the three orthogonal pick up coils, and the 3-axis magnetometer;

using the detected radio frequency pulses to synchronize measurements taken by the 3-axis magnetometer and the three orthogonal pick up coils to a time frame of a gradient driver hardware, thereby matching the measurements to a pulse sequence waveform; and combining the voltage vectors measured by the three orthogonal pick up coils and the magnetic flux vectors of the static magnetic field with the pulse sequence waveform in order to solve for the instantaneous position and orientation of the device within an imaging volume of the MRI scanner.

7. The method of claim 6 wherein data is transmitted from the device to an external processor.

8. The method of claim 7 wherein the solving for the instantaneous position and orientation of the device is done by the external processor.

9. The method of claim 6 wherein the solving for the instantaneous position and orientation of the device is done by a processor of the device.

10. The method of claim 6 further including storing data in a memory.

* * * * *